US00PP18115P2

(12) United States Plant Patent
Pan

(10) Patent No.: US PP18,115 P2
(45) Date of Patent: Oct. 9, 2007

(54) ***LANTANA* PLANT NAMED 'BANTE CHERIA'**

(50) Latin Name: *Lantana camara*
Varietal Denomination: Bante Cheria

(75) Inventor: Shifeng Pan, Hollister, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/406,007

(22) Filed: Apr. 18, 2006

(51) Int. Cl.
*A01H 5/00* (2006.01)

(52) U.S. Cl. ..... Plt./227

(58) Field of Classification Search ..... Plt./227
See application file for complete search history.

*Primary Examiner*—Kent Bell
*Assistant Examiner*—Annette H Para
(74) *Attorney, Agent, or Firm*—Jondle & Associates, P.C.

(57) ABSTRACT

A *lantana* plant particularly distinguished by mainly red to cherry-red and partly yellow to orange flowers, a continuous, abundant and mid-season flowering response, deep green foliage with ovate leaves, medium vigor, a compact and mounding plant habit and a well-branched and tight plant habit, is disclosed.

2 Drawing Sheets

Genus and species: *Lantana camara.*
Variety denomination: 'Bante Cheria'.

BACKGROUND OF THE NEW PLANT

The present invention comprises a new and distinct cultivar of *lantana,* botanically known as *Lantana camara* and hereinafter referred to by the cultivar name 'Bante Cheria'. The new cultivar originated from a hybridization made in October 2002 in Gilroy, Calif. The female parent was '22-1', a proprietary rose-flowered *lantana* plant (unpatented), while the male parent was '22-2', a proprietary fuschia-flowered *lantana* plant (unpatented).

The new cultivar was created in October 2002 in Gilroy, Calif. and has been asexually reproduced repeatedly by vegetative cuttings and tissue culture in Gilroy, Calif. over a two and one-half-year period. The plant has also been trialed at Gilroy, Calif., Andijk, The Netherlands, and Hillscheid, Germany. The present invention has been found to retain its distinctive characteristics through successive asexual propagations.

Plant Breeder's Rights for this cultivar have been applied for in Canada on Mar. 31, 2005 and with the European Union on Oct. 14, 2005.

SUMMARY OF THE INVENTION

The following are the most outstanding and distinguishing characteristics of the new cultivar when grown under normal horticultural practices in Gilroy, Calif. and Hillscheid, Germany.

1. Mainly red to cherry-red and partly yellow to orange flowers;
2. A continuous, abundant and mid-season flowering response;
3. Deep green foliage with ovate leaves;
4. Medium vigor;
5. A compact and mounding plant habit; and
6. A well-branched and tight plant habit.

DESCRIPTION OF THE PHOTOGRAPHS

This new *lantana* plant is illustrated by the accompanying photographs which show overall plant habit including blooms, buds and foliage of the plant; the colors shown are as true as can be reasonably obtained by conventional photographic procedures. The photos are of plants in a spring through fall trial setting.

DESCRIPTION OF THE NEW CULTIVAR

Figure 1:
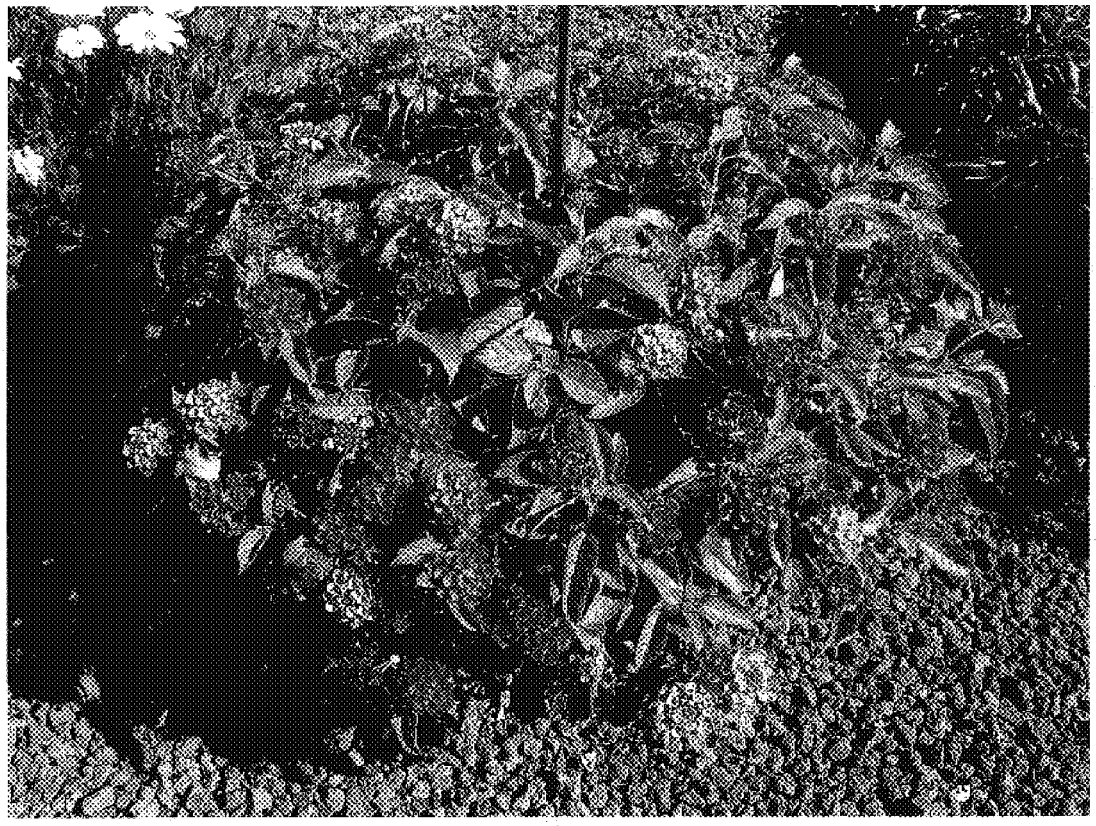
FIG. 1 shows the overall plant habit, including inflorescences, buds and foliage of three 23-week old plants in a tub.
Figure 2:
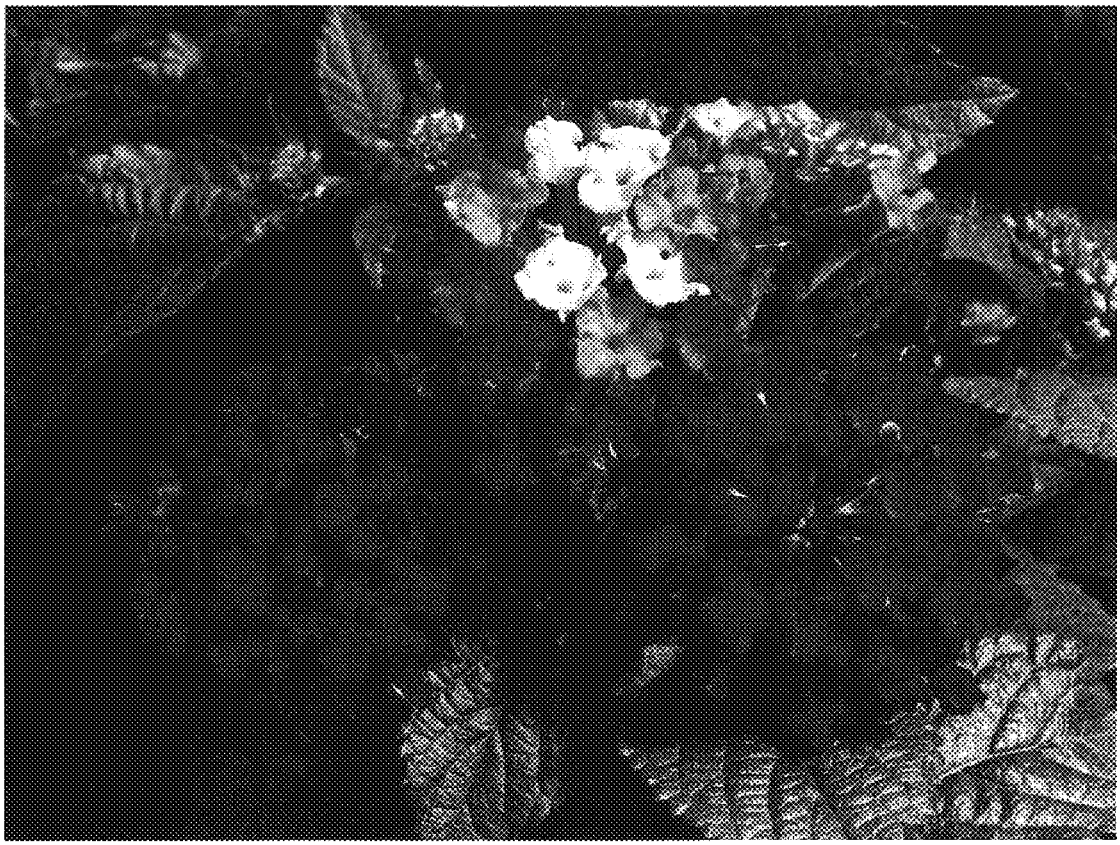
FIG. 2 shows a close-up of the mature inflorescence.

The following detailed descriptions set forth the distinctive characteristics of 'Bante Cheria'. The data which define these characteristics were collected from asexual reproductions carried out in Hillscheid, Germany. The plant history was taken on 9- to 11-week-old plants, pinched once and grown 12-cm plastic pots in a greenhouse in Hillscheid, Germany in Summer 2005. Observations were made in early September 2005 when the plants were beginning to flower. Color readings were taken under natural light. Color references are primarily to The R.H.S. Colour Chart of The Royal Horticultural Society of London (R.H.S.) (2001 edition).

DETAILED BOTANICAL DESCRIPTION

Classification:
*Family.*—Verbenaceae.
*Botanical.*—*Lantana camara.*
*Common name.*—*Lantana.*

Parentage:
*Female parent.*—'22-1', a proprietary (unpatented) rose-flowered *lantana* plant.
*Male parent.*—'22-2', a proprietary (unpatented) fuschia-flowered *lantana* plant.

Growth:

*Form.*—A shrub; the growing parts of the plant are herbaceous, while the plant base and the older stems are woody; commercially, it is grown as an annual.

*Growth and branching habit.*—Compact to mounding plant habit.

*Height* (*measured from the top of the soil*).—19.7 cm.

*Width* (*horizontal plant diameter*).—16.4 cm.

*Time to produce a finished flowering plant.*—12- to 13-cm weeks for a 12-cm pot in the Spring.

*Outdoor plant performance.*—Use in containers and hanging baskets.

*Time to initiate and develop roots.*—24 days.

*Root description.*—Fibrous and self-branching.

Stems:

*Number of branches per plant.*—6.7.

*Length.*—15 cm to 19 cm.

*Diameter* (*measured from the midpoint*).—0.3 cm; immature stems are square.

*Internode length.*—1.0 cm to 2.5 cm.

*Color.*—Immature (growing) stems: RHS 138A. Mature (woody) stems: RHS 165A with RHS 159A stripes.

*Anthocyanin.*—Absent.

*Texture.*—Setose (covered with stiff hair).

Leaves:

*Arrangement.*—Opposite and decussate.

*Fragrance.*—The foliage has a lemon-like fragrance.

*Immature leaf.*—Color: Upper surface: RHS 143B. Lower surface: Between RHS 143C and RHS 144C.

*Mature leaf.*—Color: Upper surface: Mainly RHS 137A (deep green), while older leaves are a deeper green between RHS 137A and RHS 139A. Lower surface: RHS 137D. Length: Up to 7.5 cm. Width: Up to 5.3 cm. Shape: Ovate, wide. Apex: Acute. Base: Truncate to slightly cordate. Margin: Serrate. Texture: Sparsely pubescent and somewhat glossy; lower surface is densely pubescent, setose, mainly along the leaf veins. Venation: Pinnate. Venation color: RHS 146D for the lower surface; the upper surface is indistinct.

*Petioles.*—Length: 0.5 cm to 1.5 cm. Diameter: 0.02 cm. Color: RHS 146C. Texture: Rough with short pubescence.

Flower buds:

*Shape.*—Tubular and narrow.

*Length.*—1.5 cm.

*Diameter* (*at the tip*).—Up to 0.6 cm.

*Color* (*at tight bud*).—RHS 21A at the tip, while the lower part is RHS 42A.

Inflorescence:

*Blooming habit.*—Flowers continuously from Spring through Fall; flowers appear about 12 weeks after planting of rooted cuttings; inflorescences usually appear in pairs from a nodium with one inflorescence per leaf axil.

*Fragrance.*—None.

*Inflorescence type.*—Umbel-like; flattened semi-sphere and subtended by a ring of leaflets; the florets are sessile on an ovate receptacle.

*Horizontal diameter of inflorescence.*—4.2 cm to 4.7 cm.

*Vertical depth of inflorescence.*—Up to 2.1 cm.

*Number of inflorescences per plant.*—12 to 15 (about 2 inflorescences per stem).

*Number of florets per inflorescence.*—18 to 23.

*Peduncle.*—Length: Up to 0.6 cm. Diameter: 0.2 cm to 0.25 cm. Color: RHS 143B. Texture: Covered with rough pubescence.

*Pedicels.*—None, flowers are sessile.

Flowers:

*Floret form.*—Composed of 5 petals that are mostly fused; salver-shaped to shallow cup-shaped and zygomorphic, with a relatively long tube at the base.

*Corolla diameter.*—1.0 cm to 1.3 cm.

*Floret depth.*—1.6 cm.

*Immature flower* (*face*).—Color: Upper surface: RHS 12A. Lower surface: RHS 18C.

*Mature flower* (*face*).—Color: Upper surface: Mainly bluish-red, deeper than RHS 57A, RHS 12A (yellow) and RHS 34C (orange). Lower surface: RHS 63B (purple-pink) for the margin and the main part and somewhat lighter, RHS 64D, at the center. Corolla tube: Shape: Narrow tube. Length: 1.3 cm. Diameter (at opening): 0.3 cm. Color: Outer surface: Mainly RHS 63A. Inner surface: About RHS 53C. Texture: Densely pubescent.

*Petals.*—Length of lobe: 0.3 cm to 0.4 cm. Diameter of lobe: 0.6 cm to 0.7 cm. Lobe shape: Salver-shaped. Apex: Rounded. Base: Fused. Margin: Mainly entire. Degree of lobation: Moderate. Texture: Smooth.

*Calyx. General: Composed of* 5 fused sepals forming a short tube around the base of the floret. Shape: Tube-shaped. Length: 0.3 cm. Diameter: 0.2 cm to 0.3 cm. Color: RHS 139D (pale green). Apex (of sepals): Acute. Base (of sepals): Fused. Margin (of sepals): Entire or slightly fringed. Texture: Densely pubescent.

Reproductive organs:

*Stamens.*—Quantity: 4, which protrude from the floret tube. Filament color: RHS 155A (whitish). Filament diameter: 0.1 cm. Filament length: About 0.9 cm. Anther color: RHS 1A (yellow). Anther length: 0.1 cm. Anther shape: Spindle-shaped. Pollen amount: Sparse. Pollen color: RHS 18A (yellow).

*Pistil.*—Quantity: One. Length: 0.6 cm. Style diameter: 0.1 cm. Stigma color: RHS 144C (pale-green). Style color: RHS 155A (whitish).

Fruit/seed set: Occasionally; blueberry-like fruits are formed; mature fruits are RHS N186A (black), glossy, round, slightly flattened, 0.7 cm in diameter and 0.5 cm in length.

Disease and insect resistance: None observed.

COMPARISON WITH PARENTAL AND COMMERCIAL CULTIVARS

'Bante Cheria' differs from the female parent '22-1' (unpatented) in that 'Bante Cheria' has mainly red to cherry-red and partly yellow to orange flowers, while '22-1' has rose flowers. Additionally, 'Bante Cheria' has darker green foliage and a more compact plant habit than '22-1'.

'Bante Cheria' differs from the male parent '22-2' (unpatented) in that 'Bante Cheria' has mainly red to cherry-red and partly yellow to orange flowers, while '22-2' has fuschia flowers. Additionally, 'Bante Cheria' has darker green foliage than '22-2'.

'Bante Cheria ' differs from the commercial variety 'Robcomplan' (U.S. Plant Pat. No. 9,837) in that 'Bante Cheria' has a more compact plant habit and rounder leaf shape than 'Robcomplan'. Additionally, the immature leaves of 'Bante Cheria' are lighter green than the leaves of 'Robcomplan'.

I claim:

1. A new and distinct cultivar of *lantana* plant as shown and described herein.

* * * * *